US005509896A

United States Patent [19]
Carter

[11] Patent Number: 5,509,896
[45] Date of Patent: Apr. 23, 1996

[54] ENHANCEMENT OF THROMBOLYSIS WITH EXTERNAL ULTRASOUND

[75] Inventor: Robert E. Carter, Arlington, Mass.

[73] Assignee: Coraje, Inc., San Francisco, Calif.

[21] Appl. No.: 303,858

[22] Filed: Sep. 9, 1994

[51] Int. Cl.$^6$ ................................................. A61N 1/30
[52] U.S. Cl. ........................... 604/21; 601/2; 604/22; 604/28; 604/53
[58] Field of Search .......................... 601/2; 604/21, 604/22, 27, 28, 52, 53; 606/127, 128

[56] References Cited

U.S. PATENT DOCUMENTS

| | | | |
|---|---|---|---|
| 4,931,038 | 6/1990 | Frigerio et al. | 604/22 |
| 5,018,508 | 5/1991 | Fry et al. | 601/2 |
| 5,040,587 | 8/1991 | Fatakura | 128/630 |
| 5,197,946 | 3/1993 | Tachibana | 604/22 |
| 5,318,014 | 6/1994 | Carter | 601/2 |

Primary Examiner—John D. Yasko
Assistant Examiner—Laird J. Knights
Attorney, Agent, or Firm—Walter A. Hackler

[57] ABSTRACT

Apparatus and methods are provided for enhancing the thrombolytic action of a thrombolytic agent and removing a thrombosis from a vascular system by introducing a select dose of thrombolytic agent proximate the thrombosis disposed within a vessel of a body and radiating the thrombosis with ultrasound generated exterior to the body to effect removal of the thrombosis in less time than the time required by activity of the selected dose of thrombolytic agent without the ultrasonic radiation of the thrombosis.

7 Claims, 1 Drawing Sheet

ENHANCEMENT OF THROMBOLYSIS WITH EXTERNAL ULTRASOUND

The present invention is generally related to the use of ultrasonic energy and is more particularly directed to the use of ultrasound in combination with thrombolytic agents to dissolve arterial thrombi.

It has been demonstrated that the utilization of ultrasonic waves can improve the diffusion and penetration of medicinal fluids or the like into the vascular system (see U.S. Pat. No. 5,197,946 to Tachibana). Tachibana teaches that in order to effectively enhance or improve the diffusion and penetration of a medicinal fluid, the oscillating element must be disposed at the point of injection of the medicinal fluid.

This is to be contrasted, according to Tachibana, with prior art techniques which utilize ultrasonic waves for improved diffusion and penetration of medicinal fluids in which the ultrasonic oscillating element is located outside the body and far from the distal end of the catheter wire which has difficulty in exhibiting a sufficient effect due to the damping of ultrasonic energy in the course of transmission down the catheter.

Other disadvantages in the use of a transmission wire to deliver ultrasonic energy to a thrombosis is transmission wire stiffness. Further, as the transmission wire diameter is reduced to lower the stiffness thereof, it is more difficult to deliver sufficient energy for effective removal of the thrombosis. To overcome these disadvantages, miniature ultrasonic ablation tools have been developed, utilizing ultrasonic transducers sized for arterial insertion. While these devices overcome the transmission wire difficulties, their small size severely limits the amount of ultrasonic energy available for direct mechanical action for fragmenting plaque and thrombosis and/or energy from improving diffusion and penetration of medicinal fluids as described in U.S. Pat. No. 5,197,946.

Ultrasonic apparatus has also been utilized to assist in the delivery of medicaments in specific areas of a vein. For example, U.S. Pat. No. 5,040,537 to Katakura teaches the use of injecting numerous fine capsules, with an agent being packed therein, into a patient's body and thereafter applying a shock wave to provide dominant positive pressure from outside the body to rupture the capsules dispersed in the body.

Thus, ultrasonic energy in the form of a pulsated shock wave is generated exterior to the body and imaged to selectively burst agent-containing capsules in order to selectively release the agent into the blood.

However, none of the teachings have recognized a long range, ultrasonic effect on drug effectiveness. The present invention is directed to the discovery that drug effectiveness within a vessel can be enhanced through the use of ultrasonic energy generated exterior to a body containing the vessel.

SUMMARY OF THE INVENTION

A method in accordance with the present invention utilizes the discovery of long range ultrasonic effects on drug effectiveness. Particularly, the present invention includes a method for increasing thrombolytic action of a thrombolytic agent by radiating a thrombolytic agent and thrombosis disposed within the body vessel with ultrasound generated exterior to the body vessel.

Importantly, this step is carried out during thrombolytic action by the thrombolytic agent on the thrombosis disposed within the body vessel.

This method is clearly distinguished from the prior art techniques such as taught by Katakura in U.S. Pat. No. 5,040,537, in which ultrasound generated exterior to the body vessel is used only to rupture capsules containing an active agent. Clearly, the prior art is specifically directed to the release of an active agent within a vessel, whereas the present invention is directed to enhancing, or increasing, the effect of the thrombolytic agent during its activity in dissolving, or splitting up, a thrombus. In other words, the present invention involves a phenomena of long range ultrasound enhancement of inherent drug activity.

The present invention encompasses the enhancement, or acceleration, of the activity of an thrombolytic agent and in that regard includes the steps of introducing a selected dose of thrombolytic agent proximate to a thrombosis disposed in the vessel of a body and radiating the thrombosis with ultrasound generated exterior to the body to effect removal of the thrombosis in less time than required by activity of the selected dose of thrombolytic agent without ultrasound radiation of the thrombosis.

In other words, the present invention for enhancing thrombolytic action of a thrombolytic agent includes the steps of injecting a thrombolytic agent proximate a thrombosis disposed in a vessel within a body and directing ultrasonic energy generated exterior to the body, at the thrombosis, with proximate thrombolytic agent, of sufficient energy to increase the thrombolytic action of the thrombolytic agent.

The present invention therefore also encompasses a method for removing a cardiovascular obstruction and in that regard includes the steps of delivering a thrombolytic agent proximate a cardiovascular obstruction disposed in a vessel within a body and directing ultrasonic energy, generated exterior to the body, at the cardiovascular obstruction with proximate thrombolytic agent, of sufficient energy to remove, in combination with the thrombolytic agent, the cardiovascular obstruction from the vessel.

More particularly, in accordance with the present invention, the thrombolytic agent introduced may be a any agent having suitable activity, such as, for example, streptokinase, staphlokinase, urokinase or a tissue plasminogen activator (TPA). These agents are set forth herein only by way of example and it should be appreciated that, as hereinabove recited, any thrombolytic agent may be utilized in accordance with the present invention.

Additionally, the radiation by ultrasound may include continuous or pulsed radiation. Still more particularly, by way of specific example only, the amount of streptokinase introduced may be in concentrations of less than about 2,000 μ/ml.

In conjunction with the hereinabove enumerated method defining the present invention, also encompassed is an apparatus for the removal of a cardiovascular blockage which, in combination, includes means for introducing a thrombolytic agent proximate a cardiovascular blockage, disposed in a vessel within a body, and ultrasonic means for radiating the cardiovascular blockage with proximate thrombolytic agent from a position exterior to the vessel and body.

The discovery, in accordance with the present invention as herein described, that ultrasonic energy, or ultrasound, can have a profound effect on the activity of a drug at "long range" has heretofore been unappreciated by workers in the field as represented by the hereinabove discussed prior art.

Clearly, the prior art teaches away from this discovery since prior art workers only were able to obtain enhancement for release of drugs within a vessel by proximate introduction of ultrasound, which was thought to be due to mechanical agitation of surrounding vessel walls, as pointed out by Tachibana in U.S. Pat. No. 5,197,946. It must be accepted that the mechanism taught by the Tachibana reference is not applicable to the present discovery in which it has been found that the "long range" radiation of the vessels from a point exterior to the vessel and body containing same enhances drug effectiveness.

BRIEF DESCRIPTION OF THE DRAWINGS

The advantages and features of the present invention will be better understood by the following description when considered in conjunction with the accompanying drawings in which.

DETAILED DESCRIPTION

Figure 1:
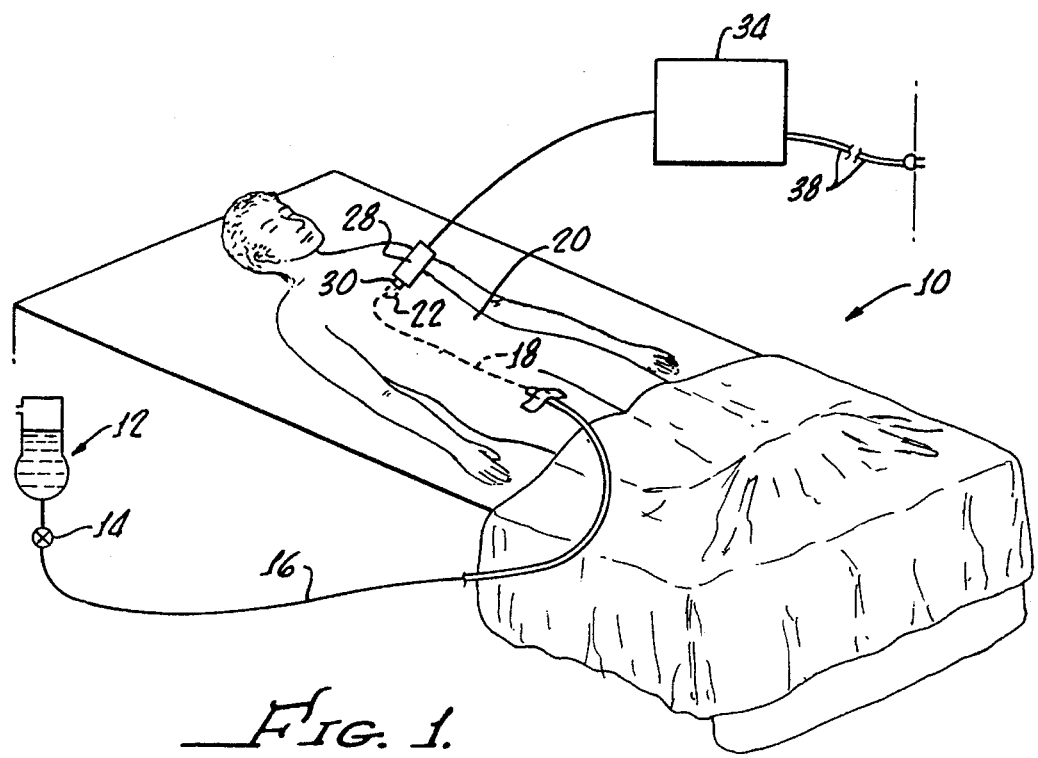
FIG. 1 is a diagram of ultrasonic surgical apparatus in accordance with the present invention or teaching method for removing a thrombosis, as well as enhancing the thrombolytic action of a thrombolytic agent.

Turning now to FIG. 1, there is shown apparatus 10 in accordance with the present invention for both removing a thrombosis and for enhancing thrombolytic action of a thrombolytic agent which may include a vial 12 of a thrombolytic agent which, by way of a valve 14 and a catheter 16, provides a means for injecting, introducing and delivering the thrombolytic agent to a vessel 18 within a body 20 proximate a thrombosis 22 illustrated by the dashed lines in FIG. 1.

Alternatively, the thrombolytic agent can be introduced or injected into the vessel 18 proximate the thrombosis in any conventional manner, including, for example, hypodermic needle or the like (not shown). Also shown in FIG. 1 is a transducer 28 having a tip positioned exterior to the body 12 and interconnected to an oscillator/driver 34 which provides means for radiating the cardiovascular blockage 30 with proximate thrombolytic agent from a position exterior to the vessel 18 and body 20.

The ultrasonic transducer 28 may be of any conventional design with a frequency range of about 19 to about 1 mHz, the frequency being manually adjustable for transmitting ultrasonic frequency through a tip 30. The frequency range may be limited to a range of between about 20 kHz and about 500 kHz if desired.

It should be appreciated that the tip 30 can include means for focusing the ultrasound as may be required in order to concentrate or specifically direct the ultrasound to a desired area or volume.

The driver is powered through conventional 110 volt line 38 and may have a power output of up to, for example, about 50 watts through a tip active area of about 0.75 inches by 0.75 inches. The power levels obtainable from the ultrasonic transducer 28 are capable of producing violent cavitation in tap water at atmospheric pressure and the limiting factor of introducing ultrasonic power into the body 20 would be possible skin irritation despite the output capability of the device. The driver 34 and transducer may be operated at a duty cycle of 100%, i.e., continuous output, or pulse-operated at, for example, a 50% duty cycle.

In accordance with the present invention, the apparatus 10 is useful in the method of the present invention for removing a thrombosis in which a selected dose of thrombolytic agent is introduced proximate the thrombosis disposed within a vessel 18 in the body 20 and a thrombosis 22 is radiated with ultrasound generated exterior to the body 20 to effect removal of the thrombosis in less time than required by activity of the selected dose of thrombolytic agent, without the ultrasound radiation of the thrombosis. Specific examples of this method will be shown in the following examples.

Preferably, the method includes the introduction of streptokinase as a thrombolytic agent into the vessel 18. As will be specifically set forth in the examples, the ultrasound may be continuously introduced or introduced in pulses, whereas the streptokinase may be introduced at concentrations of less than about 2,000 μl/ml.

In some instances, the method of the present invention not only provides enhancement, or acceleration, of the activity of the thrombolytic agent but also provides for removal of a thrombosis, utilizing a combination of the exterior radiated ultrasound and thrombolytic agent, which otherwise cannot be removed through the use of a thrombolytic agent by itself. This is specifically set forth hereinafter in the following examples.

EXAMPLE I

Experimental Setup

Ultrasound device, Piezo driver, Model CU51 - E - 001, was produced by PIEZO Systems, Inc., Cambridge, Mass. The frequency of the machine is about 26 kHz. The transducer's overall dimensions are 6.5 cm in length and 2.0 cm in diameter. The output of ultrasound energy can be adjusted by turning both the amplitude knob and frequency knob. The output of ultrasound energy can be measured by watching the Power Meter (unit: microamperes). There are no direct meters to reflect the operating frequency and operating ultrasound intensity.

Results

About 200 clots from a health researcher were used in serial in vitro studies to confirm that external ultrasound can enhance the thrombolytic action of a thrombolytic agent such as streptokinase. The results are as follows:

Clot reduction is dependent on the dosage of streptokinase. The effects of three different concentrations of streptokinase (SK) (50 μ/ml, 250 μ/l, 2,000 μ/ml) and ultrasound on one-hour old clot lysis were analyzed for thirty minutes. The results are shown in Table 1 for an ultrasound device at a power level of about 20 microamperes (pulsed mode), 40 microamperes (continuous mode), and in Table 2 for streptokinase alone.

It can be seen by comparison of Tables 1 and 2 that for a given dose of streptokinase, a significantly greater reduction in clot size (by weight percent) occurs when the clot is radiated with ultrasound for an equal period of time, 30 minutes. Therefore, a shorter length of time is required for a desired clot reduction when both ultrasound and the streptokinase are utilized as opposed to streptokinase itself.

TABLE 1

|  | USD + SK (50 μ/ml) | USD + SK (250 μ/ml) | USD + SK (2000 μ/ml) |
|---|---|---|---|
| reduction, % | 63% | 81% | 85% |
| weight reduction | 170 mg | 262 mg | 315 mg |

TABLE 2

|  | SK (50 μ/ml) | SK (250 μ/ml) | SK (2000 μ/ml) |
|---|---|---|---|
| reduction, % | 26% (n = 2) | 29 ± 6% (n = 7) | 48% (n = 2) |
| weight reduction | 48 ± 4 mg | 74 ± 24 mg | 130 ± 28 mg |

EXAMPLE II

Utilizing the sample experimental setup as in Example I, the function of clot reduction on ultrasound exposure time has been determined. With the combination of streptokinase (250 μ/ml) and ultrasound, one-hour old clot lysis were tested, using four different exposure times, 5 minutes, 10 minutes, 13 minutes and 30 minutes. The results are shown in Table 3.

TABLE 3

|  | Clot reduction rate | Clot weight reduction |
|---|---|---|
| 5 minutes subgroup(n = 1) | 30% | 30 mg |
| 10 minutes subgroup(n = 2) | 36 ± 16% | 36 ± 9 mg |
| 15 minutes subgroup(n = 8) | 46 ± 7% | 126 ± 33 mg |
| 30 minutes subgroup(n = 8) | 68 ± 9% | 211 ± 33 mg |

EXAMPLE III

Utilizing the same experimental setup as in Example I, the function of clot reduction on clot age has been determined, with 250 μ/ml streptokinase, combined with ultrasound for 30 minutes. The effect of clot age on thrombolysis is shown in Table 4.

TABLE 4

|  | Clot reduction % | Clot weight reduction |
|---|---|---|
| 1-hour old clot (n = 6) | 74 ± %9% | 217 ± 35 mg |
| 2-hour old clot (n = 5) | 68 ± 9% | 204 ± 27 mg |
| 3-hour old clot (n = 2) | 67 ± 4% | 184 ± 14 mg |

EXAMPLE IV

Utilizing the same experimental setup as in Example I, the function of thrombolysis on different clot weights has been determined with 250 μ/ml streptokinase, Combined with ultrasound for 30 minutes. The effects of 1-hour old clot weight and mass on thrombolysis is shown in Tables 5 and 6.

TABLE 5

| In lighter clot subgroup (90–126 mg): | Clot reduction % | Clot weight reduction |
|---|---|---|
| SK + USD (n = 13) | 78 ± 14% | 82 ± 12 mg |
| SK alone (n = 2) | 35 ± 4% | 55 ± 14 mg |

TABLE 6

| In heavier clot subgroup (228–357 mg): | Clot reduction % | Clot weight reduction |
|---|---|---|
| SK + USD (n = 13) | 71 ± 8% | 215 ± 34 mg |
| SK alone (n = 2) | 30 ± 5 | 90 ± 25 mg |

EXAMPLE V

Utilizing the same experimental setup as in Example I, the effect of ultrasound mode on thrombolysis has been determined. With 250 μ/ml streptokinase, the one-hour old clots were exposed to continuous and pulsed ultrasound for 30 minutes. The effect of different ultrasound modes on thrombolysis is as follows:

Continuous Mode

The average clot reduction was 78±18% (net reduction of the clot weight was 80±15 mg, n=8).

Pulsed Mode

The average clot reduction was 78±8% (net reduction of the clot weight was 84± mg, n=5).

EXAMPLE VI

Figure 2:
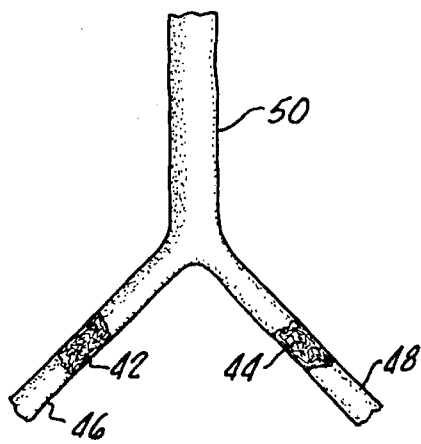
FIG. 2 is a representation of an aorta having bilateral thrombosis induced in iliofemoral arteries.

The experimental setup as in Example I has been utilized to perform experiments on two rabbits for evaluating an apparatus of the present invention which utilizes external ultrasound to remove arterial thrombi. As illustrated in FIG. 2, arterial occlusions 42, 44 were induced in bilateral iliofemoral arteries 46, 48 communicating with the aorta 50. The occlusions 42, 44 were formed by a combination of balloon abrasion followed by electrical induction of a thrombus by a guide wire (not shown). The bilateral iliofemoral thrombi were created after fifteen minutes of electrical energy to the iliofemoral arteries and the bilateral iliofemoral occlusions so formed were documented by X-ray angiography.

After formation of the occlusions, the rabbits were given low doses of streptokinase, of about 25,000 units per kilogram of rabbit weight.

Thereafter, each rabbit was exposed to ultrasound applied over the region of the iliofemoral artery occlusion by external application to the rabbit.

Both continuous ultrasound and pulsed wave ultrasound were utilized with the pulsed wave ultrasound having a duty cycle of about 30 milliseconds.

Figure 3:
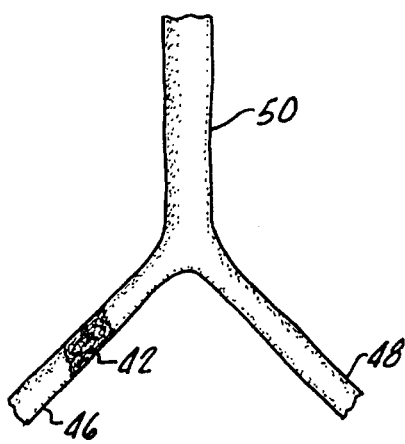
FIG. 3 is a representation similar to that shown in FIG. 2 after one of the thrombi in the iliofemoral arteries has been removed in accordance with the apparatus and method of the present invention.

Utilizing X-ray confirmation, only one occlusion 48 in iliofemoral artery was radiated by ultrasound with the other occlusion 42 in the other iliofemoral artery not being exposed to the ultrasound. After 37 minutes, at a power level of up to about 40 microamperes, the left iliofemoral thrombosis 44 exposed to the external ultrasound was completely dissolved, as illustrated in FIG. 3. In contrast, the unexposed right iliofemoral artery 46 remained totally occluded.

The same results were obtained through pulsed ultrasonic radiation except that a time of 40 minutes was required to totally remove the occlusion 44 from the artery 48, while the artery 46 remained occluded.

Although there has been hereinabove described a specific arrangement of ultrasonic apparatus and a method for thrombi dissolution in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for enhancing thrombolytic action of a thrombolytic agent, said method comprising the steps of:
   (a) injecting a thrombolytic agent proximate a thrombosis disposed in a vessel within a body; and
   (b) directing ultrasonic energy, generated exterior to the body, at the thrombosis with proximate thrombolytic agent, of sufficient energy to increase the thrombolytic action of the thrombolytic agent, said ultrasonic energy being less than about 100 Kz at less than about 50 watts power.

2. The method according to claim 1 wherein streptokinase is injected as the thrombolytic agent at a concentration of less than about 2,000 u/ml.

3. The method according to claim 1 wherein streptokinase is injected as the thrombolytic agent at a concentration of about 250 u/ml.

4. The method according to claim 1 wherein streptokinase is injected, as the thrombolytic agent at a concentration of between about 50 u/ml and about 2000 u/ml.

5. The method according to claim 3 wherein said ultrasonic energy is directed with a frequency of about 26 kHz.

6. The method according to claim 4 wherein said ultrasonic energy is directed with a frequency of about 26 kHz.

7. Apparatus for removal of a cardiovascular blockage, said apparatus comprising, in combination:

means for introducing a thrombolytic agent proximate a cardiovascular blockage disposed in a vessel within a body; and ultrasonic means for radiating the cardiovascular blockage with proximate thrombolytic agent with a frequency of less than about 100 kHz at less and 50 watts of power, said ultrasonic means being disposed exterior to the vessel and body.

* * * * *